United States Patent [19]

George et al.

[11] Patent Number: 5,229,392

[45] Date of Patent: Jul. 20, 1993

[54] 2-AMINOPYRIMIDINE-4-CARBOXAMIDE DERIVATIVES, THEIR PREPARATON AND THEIR APPLICATION IN THERAPY

[75] Inventors: Pascal George, St Arnoult en Yvelines; Philippe Manoury, Verrières le Buisson; Michel Mangane, Chatillon S/Bagneux; Jean-Pierre Merly, Sceaux, all of France

[73] Assignee: Synthelabo, Le Plessis Robinson, France

[21] Appl. No.: 872,028

[22] Filed: Apr. 23, 1992

[30] Foreign Application Priority Data

Apr. 24, 1991 [FR] France .................................. 91 05043

[51] Int. Cl.$^5$ .................. C07D 239/42; A61K 31/505
[52] U.S. Cl. ..................................... 514/275; 544/332
[58] Field of Search .......................... 544/332; 514/275

[56] References Cited

U.S. PATENT DOCUMENTS 4,849,422  7/1989  Giani et al. ......................... 514/252

Primary Examiner—John M. Ford

Attorney, Agent, or Firm—Jacobson, Price, Holman & Stern

[57] ABSTRACT

A compound which is a 2-aminopyrimidine-4-carboxamide derivative represented by general formula (I)

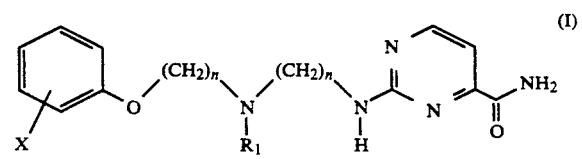

in which m represents 2 or 3, n represents 2 or 3, $R_1$ represents hydrogen or methyl, and X represents a substituent selected from the group consisting of hydrogen, fluorine, chlorine, methoxy, ethoxy, methyl and 1-methylethyl, with the proviso that more than one substituent X may be present in which case each X may be the same or different, or a pharmaceutically acceptable acid addition salt thereof.

9 Claims, No Drawings

2-AMINOPYRIMIDINE-4-CARBOXAMIDE DERIVATIVES, THEIR PREPARATON AND THEIR APPLICATION IN THERAPY

The present invention relates to 2-aminopyrimidine-4- carboxamide derivatives, to their preparation and their application in therapy.

SUMMARY OF THE INVENTION

The invention provides a compound which is a 2-aminopyrimidine-4-carboxamide derivative represented by general formula (I)

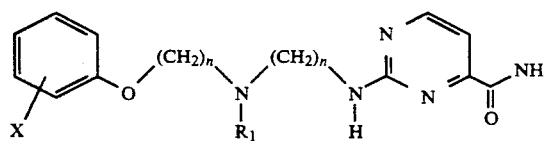

in which
- m represents 2 or 3,
- n represents 2 or 3,
- $R_1$ represents hydrogen or methyl, and
- X represents hydrogen, fluorine, chlorine, methoxy, ethoxy, methyl or 1-methylethyl, with the proviso that more than one substituent X may be present in which case each X may be the same or different, or a pharmaceutically acceptable acid addition salt thereof.

The invention also provides a process for the preparation of compounds of formula (I).

Compounds of formula (I) are useful as therapeutic substances and are antagonists of $\alpha_1$-adrenergic receptors.

DETAILED DESCRIPTION OF THE INVENTION

Preferred compounds of formula (I) are compounds wherein m+n=5. Compounds of formula (I) preferably have one or two substituents X. When one substituent X is present, it is preferably at the 2 or 4 position. When two substituents X are present, these are preferably at the 2 and 5 positions. Suitable salts of compounds of formula (I) are acid fumarates, neutral fumarates and dihydrochlorides.

According to the invention, the compounds of general formula (I) may be prepared according to the process illustrated in Scheme 1 given below.

An amine of general formula (II) (in which X, m and $R_1$ are as defined above), optionally in the form of a hydrochloride, is reacted with a halogenated reactant of general formula (III) (in which Y represents a halogen atom, R represents a group protecting the amine, for example a triphenylmethyl group, and n is as defined above). The reaction is performed in an aprotic solvent such as N,N-dimethylformamide in the presence of an inorganic base such as potassium carbonate at a temperature of 40° to 80° C.

A diamine of general formula (IV) is obtained.

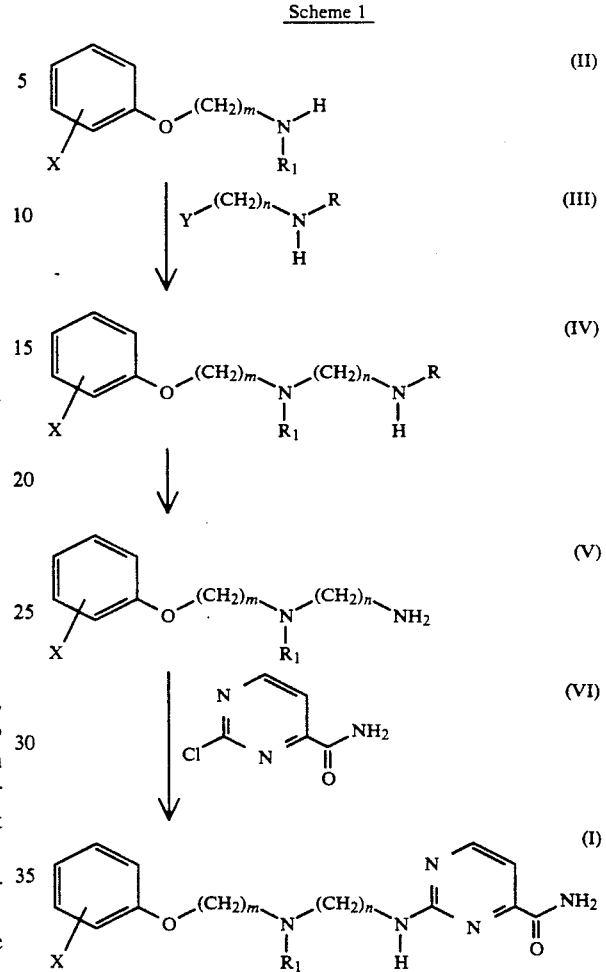

Scheme 1

The terminal alkylamine is deprotected by treatment with gaseous hydrochloric acid in an aliphatic alcohol, for example methanol, at a temperature of 0° to 60° C.

A diamine of general formula (v) is thereby obtained, which compound is reacted with 2-chloropyrimidine-4-carboxamide of formula (VI). This reaction is suitably carried out in an aprotic solvent, for example N,N-dimethylformamide, in the presence of a base, for example potassium carbonate, at a temperature of 20° to 40° C., to obtain the 2-aminopyrimidine-4-carboxamide derivative of general formula (I).

The phenoxyalkylamines of general formula (II) may be obtained by methods similar to those described in *Bull. Soc. Chim.* (1959) 839–849.

3-Bromo-N-(triphenylmethyl)propanamine of general formula III and 2-chloropyrimidine-4-carboxamide are described in patent application Ser. No. EP-0,435,749.

The halogenated reactant of general formula (III) may be prepared according to Scheme 2 given below.

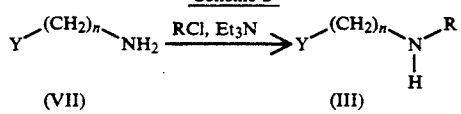

Scheme 2

A 1-haloalkylamine of general formula (VII) is reacted with a compound of formula RCl, in this instance trityl chloride (triphenylmethyl chloride), in a halogenated inert solvent such as dichloromethane, in the presence of an organic base such as triethylamine, at a temperature of 20° to 80° C.

2-Chloropyrimidine-4-carboxamide of formula (IV) may be prepared according to Scheme 3 given below.

2-Chloropyrimidine-4-carbonitrile of formula (VIII) is treated with gaseous hydrochloric acid in formic acid. 2-Chloropyrimidine-4-carbonitrile is prepared according to the method described in *J. Het. Chem.* (1964), 1, 130–133.

Scheme 3

(VIII) → (VI)
HCl gas / HCOOH

The examples which follow illustrate the preparation of a few compounds according to the invention.

The elemental microanalyses and the IR and NMR spectra confirm the structures of the products obtained.

EXAMPLE 1

2-[[3-[(2-Phenoxyethyl)amino]propyl]amino]pyrimidine-4-carboxamide (E)-2-butenedioate.

1.1. N-(2-phenoxyethyl)-N',-(triphenylmethyl)propane-1,3-diamine.

12.90 g (0.0743 mol) of 2-phenoxymethylamine hydrochloride, 31.1 g (0.0817 mol) of N-trityl-3-bromopropylamine, 25.7 g (0.186 mol) of potassium carbonate and 150 ml of N,N-dimethylformamide are introduced under argon into a 500-ml 3-necked round-bottomed flask.

The reaction mixture is stirred at 90° C. for 16 hours and then poured into ice-cold water and the resulting mixture is extracted with ethyl acetate. The organic phase is washed with water, dried and concentrated under reduced pressure. A yellow oil is obtained, which product is purified by chromatography, on a silica column with a 99:1 dichloromethane/methanol mixture (42% yield).

1.2. N-(2-phenoxyethyl)propane-1,3-diamine dihydrochloride.

12.7 g (0.029 mol) of the compound 1.1. and 350 ml of methanol are introduced into a 1—1 round-bottomed flask. Gaseous hydrochloric acid is bubbled in for 10 min while cooling with a mixture of water and ice. A clear, light yellow solution is obtained. The mixture is allowed to return to room temperature and is then brought to the refluxing temperature for 6 hours. The mixture is partially concentrated under reduced pressure to 100 ml. It is allowed to cool, and a white solid is obtained, which product is isolated by filtration followed by drying.

M.p. 274°–277° C. (96.8% yield).

1.3. 2-[[3-[(2-Phenoxy-ethyl)amino]propyl]-amino]-pyrimidine-4-carboxamide (E)-2-butenedioate.

4.0 g (0.0150 mol) of the compound 1.2., 2.4 g (0.0153 mol) of 2-chloropyrimidine-4-carboxamide, 75 ml of N,N-dimethylformamide and a little sodium iodide are introduced under argon into a 500-ml round-bottomed flask. Lastly, 7.25 g (0.0525 mol) of potassium carbonate are added and the mixture is stirred at 40° C. for 10 hours.

The reaction mixture is treated with a mixture of water and ice and extracted with ethyl acetate. The organic phase is washed with water, dried and concentrated under reduced pressure.

An oil is obtained, which product is purified by chromatography on silica with a 94:6 dichloromethane/methanol mixture. A yellow solid is obtained, which product is dissolved in ethyl acetate. The mixture is filtered and the filtrate is concentrated under reduced pressure.

The fumarate is prepared from 1.73 g (0.00549 mol) of base in 100 ml of ethanol and 0.64 g (0.00549 mol) of fumaric acid in 70 ml of ethanol. A clear, light yellow solution is obtained, which product is concentrated in the cold state to 90%. A white solid is obtained, which product is recrystallised in a 4:1 ethanol/methanol mixture (31.8% yield).

M. p. 175°–177.5° C.

EXAMPLE 2

2-[[3-[[2-(2-Methoxyphenoxy)ethyl]methyl-amino]-propyl]amino]pyrimidine-4-carboxamide (E)-2-butenedioate.

2.1. N-[2-(2-Methoxyphenoxy)ethyl]-N-methyl-N'-(triphenylmethyl)propane-1,3-diamine.

8.05 g (0.0370 mol) of N methyl-2-(2-methoxyphenoxy)-ethylamine hydrochloride, 15.5 g (0.0407 mol) of N-trityl-3- bromopropylamine, 12.78 g (0.0925 mol) of potassium carbonate and 75 ml of N,N-dimethylformamide are introduced under argon into a 500-ml 3-necked round-bottomed flask. The mixture is stirred for 15.5 hours at 90° C. The reaction mixture is treated with a mixture of water and ice and extracted with ethyl acetate. The organic phase is washed with water, dried and concentrated under reduced pressure. 18.2 g of an orange-coloured oil are obtained, which product is chromatographed on silica with a 98:2 dichloromethane/methanol mixture. 13.7 g of oil are obtained (77% yield).

2.2. N-[2-(2-Methoxyphenoxy)ethyl]-N-methylpropane-1,3-diamine.

12.9 g (0.0268 mol) of the compound 2.1. and 250 ml of methanol are introduced into a 1—1 round-bottomed flask. Gaseous hydrochloric acid is bubbled in for 15 min while cooling with a mixture of water and ice. The mixture is allowed to return to room temperature and is then brought to the refluxing temperature for 7.5 hours. The mixture is concentrated to dryness, the residue is taken up in ethanol and the mixture is concentrated again. The base is regenerated by an acid/base extraction: the oil is taken up with a mixture of water and dilute hydrochloric acid and the resulting mixture is extracted with ether. The aqueous phase is treated with sodium hydroxide and extracted with dichloromethane. The organic phase is washed with water, dried and concentrated under reduced pressure. 5.6 g of a yellow oil are obtained (87.5% yield).

2.3. 2-[[3-[[2-(2-Methoxyphenoxy)ethyl]methylamino]-propyl]amino]pyrimidine-4-carboxamide (E)-2-butenedioate.

5.55 g (0.233 mol) of the compound 2.2. , 3.75 g (0.0238 mol) of 2-chloropyrimidine-4-carboxamide, 120 ml of N,N-dimethylformamide and a few crystals of sodium iodide are introduced under argon into a 500-ml round-bottomed flask.

Lastly, 4.83 g (0.0350 mol) of potassium carbonate are added and the mixture is stirred at 50° C. for 8.5 hours.

The reaction mixture is treated with a mixture of water and ice and extracted with ethyl acetate. The organic phase is washed with water, dried and concentrated under reduced pressure.

6.0 g of a yellow oil are obtained, which product is chromatographed on silica with a 92:8 dichloromethane/methanol mixture.

The fumarate is prepared from 6.0 g (0.0167 mol) of base in 100 ml of ethanol and 1.94 g (0.0167 mol) of fumaric acid in 200 ml of ethanol.

The clear, light yellow solution is concentrated and a yellow oil is obtained. Ethyl acetate is added and the mixture is triturated in the heated state. A white solid is obtained, which product is recrystallised in ethanol (49.6% yield).

M.p. 133°–136° C.

EXAMPLE 3

2-[[3-[[3-[5-Methyl-2-(1-methylethyl)phenoxy]-propyl]-methylamino]propyl]amino]pyrimidine-4-carboxamide -2-butenedioate.

3.1. N-methyl-N-[3-[5-methyl-2-(1-methylethyl)-phenoxy]propyl]-N'-(triphenylmethyl)propane-1,3-diamine.

8.6 g (0.0334 mol) of N-methyl-3-[5-methyl-2-(1-methylethyl)phenoxy]propylamine hydrochloride, 14.0 g (0.0367 mol) of N-trityl-3-bromopropylamine, 11.55 g (0.0835 mol) of potassium carbonate and 70 ml of N,N-dimethylformamide are introduced under argon into a 500-ml 3-necked round-bottomed flask.

The reaction mixture is stirred at 90°–100° C. for 15.5 hours, then treated with a mixture of water and ice and extracted with ethyl acetate. The organic phase is washed with water, dried and concentrated under reduced pressure. A yellow oil is obtained, which product is chromatographed on silica with a 9:1 dichloromethane/methanol mixture (54.6% yield).

3.2. N-Methyl-N-[3-[5-methyl-2-(1-methylethyl)-phenoxy]propyl]propane-1,3-diamine dihydrochloride.

9.3 g (0.0179 mol) of the compound 3.1. and 180 ml of methanol are introduced into a 500-ml round-bottomed flask. Gaseous hydrochloric acid is bubbled in for 20 min while cooling with a mixture of water and ice. The reaction mixture is allowed to return to room temperature and is then brought to the refluxing temperature for 7 hours. The mixture is concentrated to dryness, and an oily, cream-coloured solid is obtained, which product is taken up in ethanol. The mixture is concentrated again, to 90%. A yellow oil is obtained, to which ethyl acetate is added, and the mixture is triturated. An amorphous white solid is obtained (90.5% yield).

3.3. 2-[[3-[[3-[5-Methyl-2-(1-methylethyl)phenoxy]-propyl]methylamino]propyl]amino]pyrimidine-4-carboxamide (E)-2-butenedioate.

5.6 g (0.0159 mol) of the compound 3.2., 2.6 g (0.0164 mol) of 2-chloropyrimidine-4-carboxamide, 80 ml of N,N-dimethylformamide and a few crystals of sodium iodide are introduced under argon into a 500-ml 3-necked round-bottomed flask. Lastly, 7.7 g (0.0557 mol) of potassium carbonate are added, and the reaction mixture is stirred at 50° C. for 8.5 hours and then treated with a mixture of water and ice. The resulting mixture is extracted with ethyl acetate, and the organic phase is washed with water, dried and concentrated under reduced pressure. A yellow oil is obtained, which product is used as it is.

Fumarate is prepared from 6.3 g (0.0158 mol) of base in 100 ml of ethanol and 1.83 g (0.0158 mol) of fumaric acid in 180 ml of ethanol. The clear solution obtained is concentrated almost completely, ethyl acetate is added and the mixture is triturated. A white solid is obtained, which product is recrystallised in ethanol (68.3% yield).

M.p. 152.5°–154.5° C.

The table which follows illustrates the physical properties of a few compounds according to the invention.

In the "salt" column, "fum." denotes an acid fumarate, "½fum." denotes a neutral fumarate and 2HCl denotes a dihydrochloride.

TABLE (I) Structure: phenyl(X)-O-(CH$_2$)$_m$-N(R$_1$)-(CH$_2$)$_n$-NH-C(=N)-pyrimidine-C(=O)NH$_2$

| No. | X | m | n | R$_1$ | Salt | M.p. (°C.) |
|---|---|---|---|---|---|---|
| 1 | H | 2 | 3 | H | fum. | 175–177.5 |
| 2 | H | 2 | 3 | CH$_3$ | fum. | 149–151.5 |
| 3 | 2-OCH$_3$ | 2 | 3 | H | fum. | 158.5–161 |
| 4 | 2-OCH$_3$ | 2 | 3 | CH$_3$ | fum. | 133–136 |
| 5 | 2-OCH$_3$, 5-Cl | 2 | 3 | H | ½ fum. | 179.5–182 |
| 6 | 2-OCH$_3$, 5-Cl | 2 | 3 | CH$_3$ | fum. | 157.5–160 |
| 7 | 2-iC$_3$H$_7$ | 2 | 3 | H | fum. | 175–178 |
| 8 | 2-iC$_3$H$_7$ | 2 | 3 | CH$_3$ | fum. | 146–149 |
| 9 | 2-iC$_3$H$_7$, 5-CH$_3$ | 2 | 3 | H | fum. | 186–188.5 |
| 10 | 2-iC$_3$H$_7$, 5-CH$_3$ | 2 | 3 | CH$_3$ | 2HCl | 141–142 |
| 11 | 2-iC$_3$H$_7$, 5-CH$_3$ | 3 | 3 | CH$_3$ | fum. | 152.5–154.5 |
| 12 | 4-F | 2 | 3 | H | fum. | 164.5–167 |
| 13 | 4-F | 2 | 3 | CH$_3$ | fum. | 140–142 |
| 14 | 2-OCH$_3$, 5-F | 2 | 3 | CH$_3$ | fum. | 129.5–132.5 |
| 15 | 4-F | 3 | 2 | CH$_3$ | fum. | 166–169 |
| 16 | 2-iC$_3$H$_7$, 5-CH$_3$ | 3 | 2 | CH$_3$ | fum. | 199–202 |
| 17 | 2-OCH$_3$, 5-F | 2 | 3 | H | fum. | 171–173 |
| 18 | 2-OC$_2$H$_5$ | 2 | 3 | CH$_3$ | fum. | 123–125.5 |

The compound of the invention were subjected to studies in respect of their antagonist activity towards $\alpha_1$-adrenergic receptors in the lower urinary tract.

Their in vitro activity was studied on isolated rabbit urethra.

Rings of adult rabbit urethra are prepared according to the method of Ueda et. al., *Eur. J. Pharmacol.*, (1984), 103, 249–254, and then, after noradrenaline sensitisation, the phenylephrine concentration-response curve is determined in the absence and in the presence of test compound.

The potency of the $\alpha_1$-adrenergic antagonism of each compound is evaluated by calculation of the pA$_2$, the antilogarithm of the molar concentration of antagonist in the presence of which the agonist concentration must be doubled in order to produce the same effect as in its absence.

The pA$_2$ values of the compounds are of the order of 5.5 to 9.

The in vivo activity of the compounds of the invention was studied in respect of their effect on urethral hypertonia produced by stimulation of the sympathetic fibres of the hypogastric nerve in anaesthetized cats.

Adult male cats are anaesthetized with pentobarbital sodium and prepared according to the method of Theobald, *J. Auton. Pharmac.*, (1983), 3, 235–239, in order to obtain a urethral hypertonia by stimulation of the sympathetic fibres of the hypogastric nerve. The contractile responses of the urethra to electrical stimulation of the hypogastric nerve are noted before and after intravenous administration of the test compounds, at cumulative doses from 1 to 1000 µg/kg.

The potency of the $\alpha_1$-adrenergic antagonism of each compound is evaluated by calculation of the $ID_{50}$, the dose which inhibits urethral hypertonia by 50%.

The $ID_{50}$ values of the compounds of the invention are of the order of 0.01 to 3 mg/kg.

The results of the tests show that the compounds of the invention display, in vitro, an antagonist activity towards the $\alpha_1$-adrenergic receptors of the smooth muscles of the lower adrenergic agonist (phenylephrine). In vivo, they inhibit urethral hypertonia produced by sympathetic nerve stimulation.

The compounds of the invention may hence be used for the symptomatic treatment of diseases and conditions involving a hyperactivity of the $\alpha$-adrenergic system in the lower urinary tract, and in particular for the treatment of benign hypertrophy of the prostate, dysuria and pollakiuria.

For this purpose, they may be presented in all forms suited to enteral or parenteral administration, combined with pharmaceutical excipients, for example in the form of tablets, dragees, capsules including hard gelatin capsules, solutions or suspensions to be taken orally or injected, and suppositories, the concentrations being such as to permit a daily dose of 0.5 to 100 mg of active substance.

We claim:

1. A compound which is a 2-aminopyrimidine-4-carboxamide derivative represented by general formula (I)

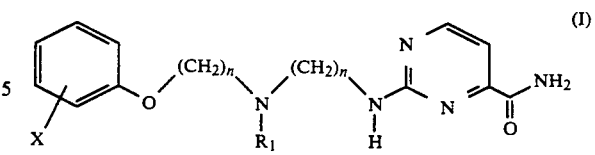

in which
m represents 2 or 3,
n represents 2 or 3,
$R_1$ represents hydrogen or methyl, and
X represents a substituent selected from the group consisting of hydrogen, fluorine, chlorine, methoxy, ethoxy, methyl and 1-methylethyl, with the proviso that more than one substituent X may be present in which case each X may be the same or different, or a pharmaceutically acceptable acid addition salt thereof.

2. A compound according to claim 1 wherein m+n=5.

3. A compound according to claim 1 wherein one or two substituents X are present.

4. A compound according to claim 1 wherein X is at the 2 or 4 position.

5. A compound according to claim 1 wherein two substituents X are present at the 2 and 5 positions.

6. A salt according to claim 1 selected from the group consisting of an acid fumarate, a neutral fumarate and a dihydrochloride.

7. 2-[[3-[[2-(2-Methoxyphenoxy)ethyl]-methylamino]propyl]amino]pyrimidine-4-carboxamide.

8. A pharmaceutical composition comprising an effective amount of a compound as claimed in claim 1 for treating a disorder of the lower urinary tract, and a pharmaceutically acceptable excipient.

9. A method of treatment of disorders of the lower urinary tract which comprises administering to a patient an effective amount of a compound as claimed in claim 1.

* * * * *